United States Patent
Lee et al.

(10) Patent No.: US 10,761,101 B2
(45) Date of Patent: Sep. 1, 2020

(54) TEST APPARATUS AND TARGET MEASUREMENT METHOD USING THE SAME

(71) Applicant: SAMSUNG ELECTRONICS CO., LTD., Suwon-si (KR)

(72) Inventors: Sung Hwa Lee, Anyang-Si (KR); Takayuki Taguchi, Osaka (JP); Hye Kyung Park, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 473 days.

(21) Appl. No.: 15/683,365

(22) Filed: Aug. 22, 2017

(65) Prior Publication Data
US 2017/0350904 A1   Dec. 7, 2017

Related U.S. Application Data

(62) Division of application No. 14/145,173, filed on Dec. 31, 2013, now abandoned.

(30) Foreign Application Priority Data

Jan. 9, 2013   (KR) .................. 10-2013-0002657

(51) Int. Cl.
*G01N 33/72* (2006.01)

(52) U.S. Cl.
CPC ......... *G01N 33/721* (2013.01); *G01N 33/726* (2013.01)

(58) Field of Classification Search
CPC ..................... G01N 33/721; G01N 33/726
See application file for complete search history.

(56) References Cited

U.S. PATENT DOCUMENTS

| | | | |
|---|---|---|---|
| 2003/0027347 A1* | 2/2003 | Shapiro | G01N 33/721 436/66 |
| 2007/0222973 A1* | 9/2007 | Hoshiko | G01N 21/82 356/39 |
| 2010/0196945 A1 | 8/2010 | Forsell | |

FOREIGN PATENT DOCUMENTS

| JP | WO2010010881 A1 | 1/2012 |
|---|---|---|
| WO | 2011/148280 A1 | 12/2011 |
| WO | 2011148280 A1 | 12/2011 |

OTHER PUBLICATIONS

Communication dated Mar. 6, 2019, issued by the Korean Intellectual Property Office in corresponding Korean Application No. 10-2013-0002657.
Office Action issued in parent U.S. Appl. No. 14/145,173 dated Nov. 18, 2016.
Office Action issued in parent U.S. Appl. No. 14/145,173 dated May 23, 2017.

* cited by examiner

*Primary Examiner* — Brian R Gordon
*Assistant Examiner* — Dwan A Gerido
(74) *Attorney, Agent, or Firm* — Sughrue Mion, PLLC

(57) ABSTRACT

A test apparatus and method for measuring a concentration of a target by correcting for an impact of hemoglobin are provided. The target measurement method includes measuring an absorbance of hemoglobin in a sample, measuring an absorbance of a target in the sample, determining variation of the absorbance of the target according to the measured absorbance of the hemoglobin, and correcting the absorbance of the target by subtracting the determined variation of the absorbance of the target from the measured absorbance of the target.

13 Claims, 6 Drawing Sheets

TEST APPARATUS AND TARGET MEASUREMENT METHOD USING THE SAME

CROSS-REFERENCE TO RELATED APPLICATION(S)

This application is a Divisional Application of U.S. application Ser. No. 14/145,173 filed Dec. 31, 2013, which claims priority from Korean Patent Application No. 10-2013-0002657, filed on Jan. 9, 2013 in the Korean Intellectual Property Office, the disclosures of which are incorporated herein by reference.

BACKGROUND

1. Field

Apparatuses and methods consistent with exemplary embodiments relate to a test apparatus and method for measurement of a target in a biochemical sample.

2. Description of the Related Art

Health conditions may be diagnosed by measuring the concentration of a specific component in blood. For example, blood plasma or serum is separated from blood, the blood plasma or serum is reacted with a reagent that is responsive to a specific component in blood to obtain reaction results, and the concentration of the specific component is measured based on the reaction results.

In this regard, several components among various components in blood are known to affect the reliability of measurement of concentrations of the other components.

For example, it is known that, when hemoglobin is present in blood plasma or serum at a certain concentration or higher due to hemolysis or the like, the concentration of a specific component to be detected is higher than an actual value thereof.

Therefore, there is a need to address this problem to obtain reliable blood test results.

SUMMARY

Exemplary embodiments provide a method of accurately measuring concentration of a target by correcting for an impact of hemoglobin.

In accordance with an aspect of an exemplary embodiment, there is provided a target measurement method including measuring an absorbance of hemoglobin in a sample, measuring an absorbance of a target in the sample, determining a variation of the absorbance of the target according to the measured absorbance of the hemoglobin, and correcting the absorbance of the target by subtracting the determined variation of the absorbance of the target from the measured absorbance of the target.

The measuring of the absorbance of hemoglobin may include irradiating the sample with light to measure absorbance of the sample and calculating the absorbance of hemoglobin in the sample based on the measured absorbance of the sample and a pre-stored equation for calculation of the absorbance of the hemoglobin.

The irradiating of the sample may include measuring the absorbance of the sample by irradiating a sample accommodated in a chamber of a reactor, excluding a reagent for detection of the target, with light having at least one predetermined wavelength.

The wavelength of light irradiated to the sample may include 450 nm, 535 nm, and 630 nm.

The reactor may include at least one reaction chamber accommodating a reagent for detection of at least one target in the sample and a control chamber excluding the reagent.

The calculating of the absorbance of the hemoglobin may include calculating the absorbance of the hemoglobin based on the pre-stored equation for calculation of the absorbance of the hemoglobin independently from change in concentration of the target, when measurement results of the absorbance of the sample are input.

The equation may include a variable to be substituted with absorbance obtained by irradiating the sample accommodated in the control chamber with light having at least one predetermined wavelength and a coefficient for calculation of the absorbance of the hemoglobin independently from change in concentration of the target.

The measuring of the absorbance of the target may include measuring the absorbance of the target in the sample by irradiating the sample accommodated in a chamber of a reactor, containing a reagent for detection of the target, with light having at least one predetermined wavelength.

The calculating of the variation of the absorbance of the target may include calculating the variation of the absorbance of the target according to the measured absorbance of the hemoglobin based on a pre-stored correlation showing the variation of the absorbance of the target according to the absorbance of the hemoglobin.

The target measurement method may further include calculating a concentration of the target based on the corrected absorbance of the target after the absorbance of the target is corrected.

The sample may include blood plasma or serum.

In accordance with an aspect of another exemplary embodiment, there is provided a test apparatus includes a light detection module to irradiate a sample with light and detect light having passed through the sample and a controller to measure absorbance of hemoglobin or a target in the sample based on detection results of the light detection module, to calculate variation of the absorbance of the target according to the measured absorbance of the hemoglobin, and to correct the absorbance of the target by subtracting the calculated variation of the absorbance of the target from the measured absorbance of the target.

The controller may control the light detection module to irradiate a sample accommodated in a chamber of a reactor, excluding a reagent for detection of the target, with light having at least one predetermined wavelength, and calculate the absorbance of the hemoglobin independently from change in concentration of the target, based on a pre-stored equation for calculation of the absorbance of the hemoglobin, when the light detection module detects the light.

The wavelength of light irradiated from the light detection module may be 450 nm, 535 nm, and 630 nm.

The reactor may include at least one reaction chamber accommodating a reagent for detection of at least one target in the sample and a control chamber excluding the reagent.

The equation may include a variable to be substituted with absorbance obtained by irradiating the sample accommodated in the control chamber with light having at least one predetermined wavelength and a coefficient for calculation of the absorbance of the hemoglobin independently from change in concentration of the target.

The controller may control the light detection module to irradiate a sample accommodated in a chamber of a reactor, containing a reagent for detection of the target, with light having at least one predetermined wavelength, and measure the absorbance of the target in the sample based on detection results when the light detection module detects the light.

The controller may calculate variation of the absorbance of the target according to the measured absorbance of the hemoglobin based on a pre-stored correlation showing the variation of the absorbance of the target according to the absorbance of the hemoglobin.

The correlation may be calculated based on measurement results of absorbance of a target in each of a plurality of samples having the same concentration of the target and different concentrations of the hemoglobin.

The controller may calculate a concentration of the target based on the corrected absorbance of the target when the absorbance of the target is corrected.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION OF EXEMPLARY EMBODIMENTS

Figure 1:
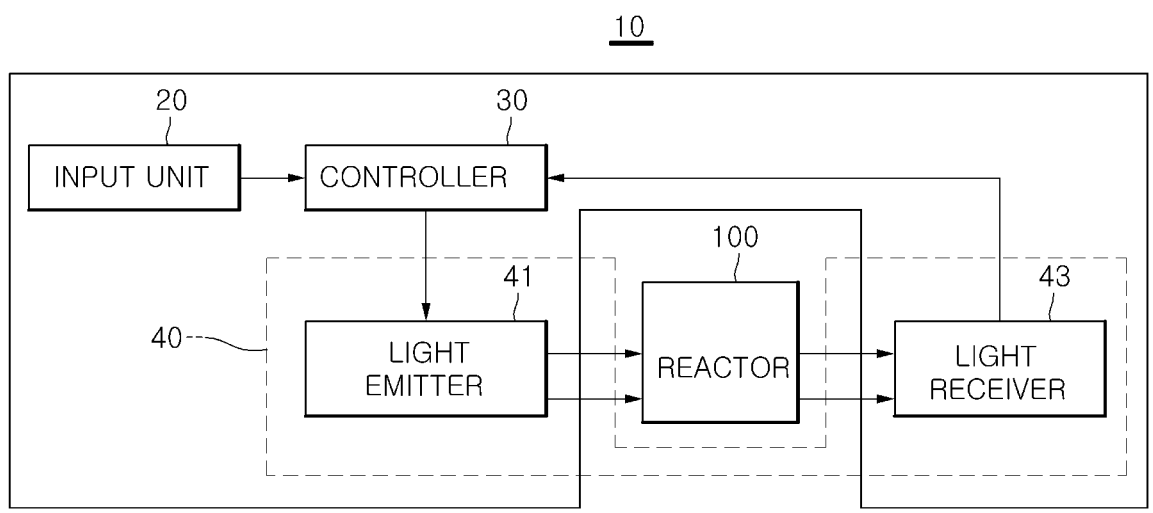
FIG. 1 is a block diagram illustrating a structure of a test apparatus according to an exemplary embodiment.

Reference will now be made in detail to exemplary embodiments, examples of which are illustrated in the accompanying drawings, wherein like reference numerals refer to like elements throughout.

Hereinafter, exemplary embodiments will be described in detail with reference to the accompanying drawings.

FIG. 1 is a block diagram illustrating a structure of a test apparatus 10 according to an exemplary embodiment.

Referring to FIG. 1, the test apparatus 10 includes an input unit 20 through which a user command is input from the outside, a controller 30 to control operations and functions of the test apparatus 10 in accordance with user commands input through the input unit 20 and measure the concentration of a target in a sample, a storage unit (not shown) to pre-store information needed to measure the concentration of the target, and a light detection module 40 including a light emitter 41 to emit light which irradiates a sample accommodated in a reactor 100 and a light receiver 43 to detect light that has passed through the sample or has been reflected from the sample after being irradiated by the light emitter 41.

The reactor 100 accommodates a biochemical sample, such as blood, and allows occurrence of a biochemical reaction to identify the presence or absence of the target contained in the sample or calculate the concentration of the target. The reactor 100 may include a reagent or the like to detect the target through reaction with the target.

The reactor 100 may include a microfluidic device or a fluidic analysis cartridge to transfer a fluid by centrifugal force or capillary force as driving pressure. Hereinafter, a fluidic analysis cartridge will be described as an example of the reactor 100.

The light emitter 41 of the light detection module 40 may be realized as a surface light source that has a wide light emitting area and is capable of irradiating uniform light so as to irradiate light to a certain region of the reactor 100. For example, a backlight unit may be used as the light emitter 41.

The light emitter 41, which is a light source that is turned on and off at a predetermined frequency, may include a semiconductor light emitting diode (LED) such as an LED or a laser diode (LD), or a gas discharge lamp such as a halogen lamp or a xenon lamp. Alternatively, the light emitter 41 may be realized as a surface light source that has a wide light emitting area and is capable of irradiating uniform light so as to irradiate light to a certain region of the fluidic analysis cartridge 100. For example, a backlight unit may be used as the light emitter 41.

The light receiver 43 of the light detection module 40 may detect light that has passed through the sample of the reactor 100 or has been reflected from the sample thereof after being irradiated from the light emitter 41 to generate an electrical signal corresponding to the intensity of the light. The light receiver 43 may include a depletion layer photodiode, an avalanche photodiode, a photomultiplier tube, or the like. In addition, the light receiver 43 may be realized as a CMOS image sensor or a CCD image sensor.

The light emitter 41 and the light receiver 43 may be provided on opposite sides with the reactor 100 so as to face each other or disposed together above or below the reactor 100. In the illustrated exemplary embodiment, the light emitter 41 and the light receiver 43 face each other with the reactor 100 interposed therebetween.

The intensity or wavelength of light emitted from the light emitter 41 may be controlled according to a command from the controller 30.

The controller 30 implements a process of minimizing an impact of hemoglobin by correcting detection results when identifying the presence or absence of the target contained in the sample or detecting the concentration of the target, to prevent distortion of results due to the impact of hemoglobin that may be contained in the sample due to hemolysis.

The target may be variously determined according to items to be identified through a blood test. In the exemplary embodiment, total bilirubin (TBIL) is used as a test item and bilirubin is used as a target. The test item and the target are for illustrative purposes only and are not limited to the above examples. That is, exemplary embodiments may include various test items and targets.

The sample may include blood plasma or serum obtained by removing red and white blood cells from blood. In the exemplary embodiment, serum is used as the sample.

The controller 30 measures absorbance of hemoglobin present in serum contained in the fluidic analysis cartridge 100.

Figure 2:
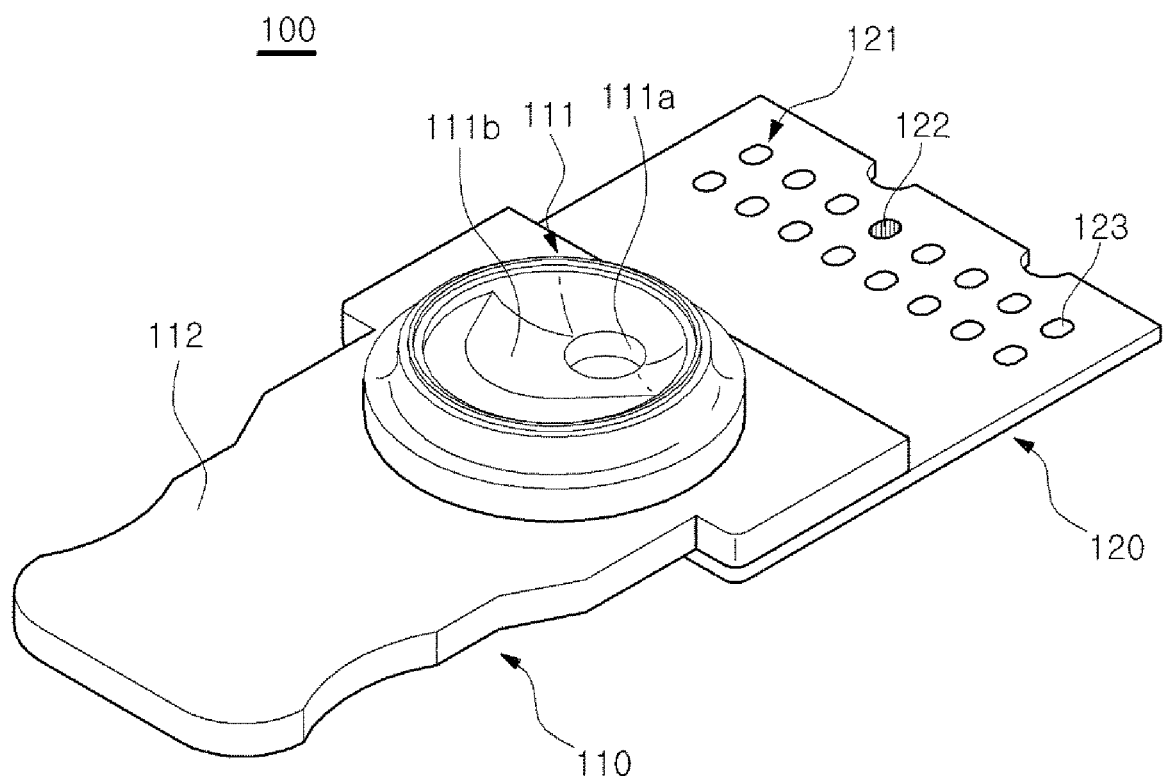
FIG. 2 is a perspective view of a fluidic analysis cartridge of the test apparatus of FIG. 1.

FIG. 2 is a perspective view of the fluidic analysis cartridge 100 of the test apparatus 10 of FIG. 1.

The fluidic analysis cartridge 100 includes a housing 110 to support the fluidic analysis cartridge 100 and a test unit 120 in which a reaction occurs between a fluid and a reagent.

The housing 110 includes a holding part 112 configured to be held by a user and a fluid accommodation part 111 to accommodate the fluid. The fluid accommodation part 111 may include a hole 111a through which the fluid is introduced and a supply auxiliary part 111b inclined to guide the fluid to the hole 110a. A filter may be provided in the hole 110a to remove corpuscles from blood when blood is introduced. The test unit 120 includes a plurality of chambers 121 to accommodate the fluid introduced through the fluid accommodation part 111.

When blood is introduced, generally, blood is loaded in the hole 111a and pressure is applied thereto to filter the blood to remove corpuscles and, in this process, red blood cells are broken and hemoglobin in the red blood cells is introduced into serum. The introduced hemoglobin distorts test results. Thus, to correct for an impact of the hemoglobin, in the exemplary embodiment, absorbance of the hemoglobin introduced into serum is measured to calculate concentration of the hemoglobin.

The chambers 121 of the test unit 120 include reaction chambers 122 to accommodate reagents for detection of various types of targets and a control chamber 123 that does not include a reagent for detection of a target. Any one of the reaction chambers 122 may include a reagent for detection of TBIL, which is one of the test items.

The serum is transferred to the reaction chamber 122 containing a reagent for measurement of TBIL and the control chamber 123, and the controller 30 measures absorbance of the serum by irradiating the control chamber 123 with light, to measure the concentration of the hemoglobin.

The controller 30 controls the light emitter 41 of the light detection module 40 to irradiate the control chamber 123 with light having a predetermined wavelength. The light emitter 41 irradiates the control chamber 123 containing the serum with light having at least one wavelength selected from among 450 nm, 535 nm, and 630 nm under control of the controller 30. Wavelengths of irradiated light are not limited to the above-described wavelengths. That is, light having any other wavelengths may be irradiated so long as a reagent is responsive to the wavelength. The same applies throughout the specification.

The light receiver 43 of the light detection module 40 detects light that has passed through the serum contained in the control chamber 123 and transmits detection results to the controller 30, and then the controller 30 calculates the absorbance of the hemoglobin based on the detection results.

The controller 30 uses an equation for calculating the absorbance of the hemoglobin to calculate the absorbance of the hemoglobin. In this regard, the equation is predetermined through experiments and stored in the storage unit.

The serum contains a target as well as hemoglobin and thus the absorbance of the hemoglobin is affected by the concentration of the target. If the absorbance of the hemoglobin used to calculate the concentration of the hemoglobin varies according to change in concentration of the target contained in the serum even though the serum contains the same concentration of hemoglobin, the results are not reliable.

Thus, the controller 30 calculates the absorbance of the hemoglobin from which impact due to change in concentration of the target is maximally excluded, by applying the detection results of the light detection module 40 to the equation for calculating the absorbance of the hemoglobin.

The equation for calculating the absorbance of the hemoglobin may be determined through the following processes.

Control serums that do not contain hemoglobin and contain different concentrations of TBIL are diluted with different concentrations of hemoglobin to prepare a plurality of serums containing different concentration combinations of hemoglobin and TBIL.

The prepared serums are irradiated with light having wavelengths of 450 nm, 535 nm, and 630 nm to measure absorbances of the serums according to the concentration of the hemoglobin.

Figure 3:
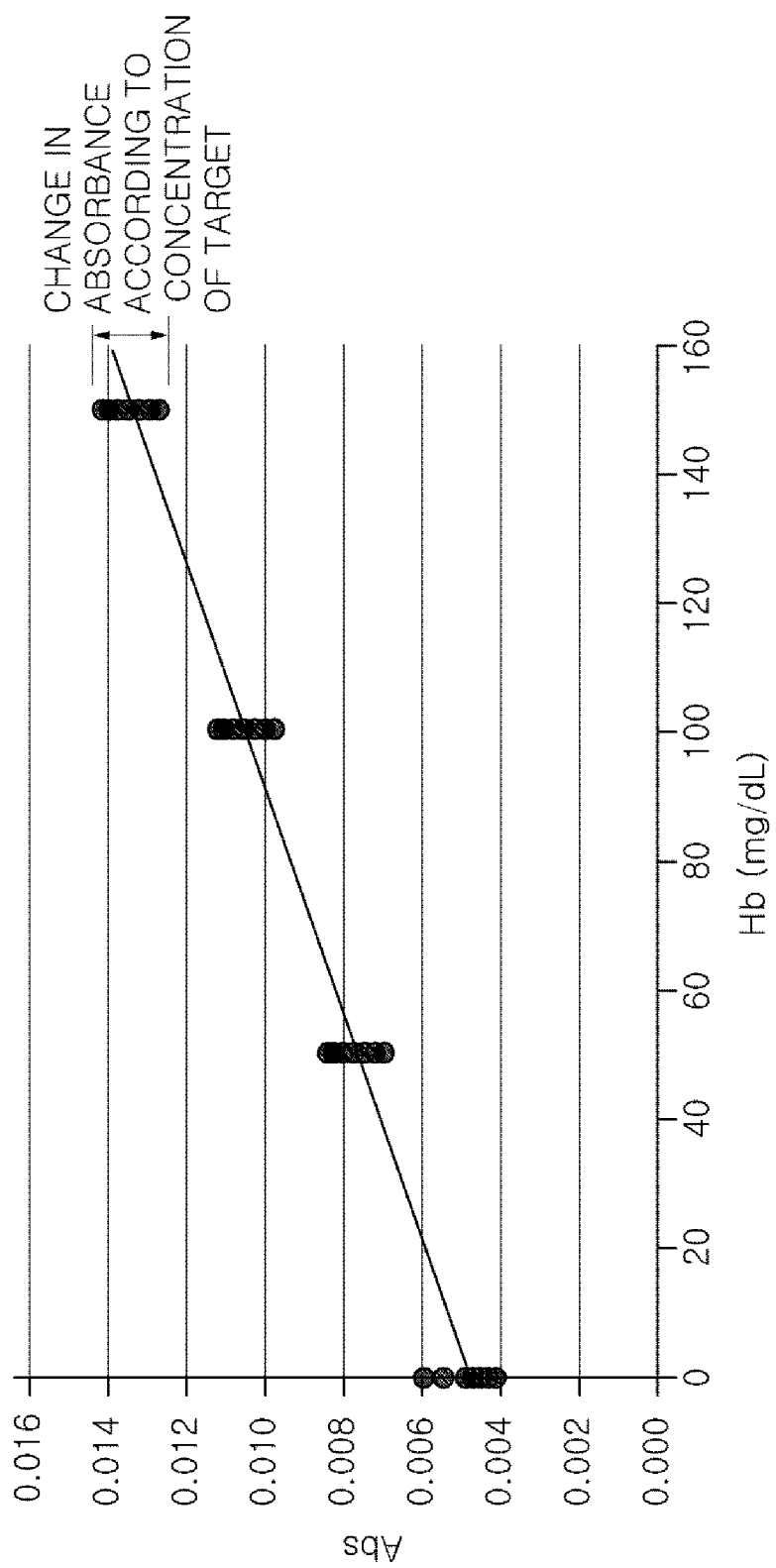
FIG. 3 is a graph showing change in absorbance of a sample according to change in concentrations of hemoglobin and a target.

FIG. 3 is a graph showing change in absorbances of the serums according to change in concentration of hemoglobin, which is calculated through the above-described process.

Referring to FIG. 3, it can be confirmed that the absorbances of the serums increase as the concentration of the hemoglobin increases and, although the change is small, the absorbances of the serums vary according to change in concentration of the TBIL.

The absorbance of the hemoglobin may be calculated using Equation 1 below.

[Equation 1]

$$Hb(abs) = SB(535\ nm) - SB(630\ nm) - \{SB(450\ nm) - SB(630\ nm)\} * a$$

In Equation 1, Hb(abs) denotes the absorbance of the hemoglobin, and serum blank SB( . . . nm) denotes absorbance of wavelengths of light of the control chamber 123.

In this regard, change in absorbance of the hemoglobin according to impact of the target may be minimized by adjusting a coefficient "a" which is multiplied by a difference between the absorbance of light having a wavelength of 450 nm and the absorbance of light having a wavelength of 630 nm.

As a result of experimentation, when change in absorbances of the serums according to change in concentration of the target is the smallest, the coefficient a is 0.143.

The controller 30 may calculate the absorbance of the hemoglobin that is minimally affected by the target by applying the absorbance of the control chamber 123 which is detected by the light receiver 43 of the light detection module 40 to the equation for calculating the absorbance of the hemoglobin represented by Equation 1 above.

The controller 30 measures the absorbance of serum by irradiating the reaction chamber 122 containing a reagent for measurement of TBIL with light, to measure the absorbance of a target contained in the serum.

The controller 30 controls the light emitter 41 of the light detection module 40 to irradiate the reaction chamber 122 containing a reagent for measurement of TBIL with light having a predetermined wavelength. The light emitter 41 irradiates the reaction chamber 122 with light having at least one wavelength selected from among 450 nm, 535 nm, and 630 nm under control of the controller 30.

The light receiver 43 of the light detection module 40 detects light that has passed through serum accommodated in the reaction chamber 122 and transmits detection results, and then the controller 30 calculates the absorbance of the target based on the detection results.

The calculated absorbance of the target includes an impact of the hemoglobin and thus is subjected to a correction process for removal of the impact of the hemoglobin to obtain accurate results.

The controller 30 calculates variation of the absorbance of the target according to the absorbance of the hemoglobin, which is obtained through the above-described process.

The storage unit may pre-store a correlation between the variation of the absorbance of the target and the absorbance of the hemoglobin. The controller 30 calculates the variation of the absorbance of the hemoglobin by applying the calculated absorbance of the hemoglobin to the correlation stored in the storage unit.

The correlation may be predetermined through the following processes.

Control serums that do not contain hemoglobin and contain TBIL at the same concentration are diluted with different concentrations of hemoglobin to prepare a plurality of serums containing different concentrations of hemoglobin. The prepared serums are selectively irradiated with light having wavelengths of 450 nm, 535 nm, and 630 nm used in TBIL test to measure absorbance of the TBIL.

The prepared serums are selectively irradiated with light having wavelengths of 450 nm, 535 nm, and 630 nm used in TBIL test to measure the absorbance of the TBIL.

The absorbance of the TBIL may be calculated using Equation 2 below.

[Equation 2]

$$TBIL(abs) = \{SB(450\ nm) - SB(535\ nm)\} - \{TBIL(450\ nm) - TBIL(535\ nm)\}$$

In Equation 2, TBIL(abs) denotes the absorbance of TBIL, SB( . . . nm) denotes absorbance of wavelengths of light of serum accommodated in the control chamber 123, and TBIL( . . . nm) denotes absorbance of wavelengths of light of serum accommodated in the reaction chamber 122 containing a reagent for measurement of TBIL.

Through data of the absorbance of the TBIL of each serum calculated using Equation 2, variation of the absorbance of the TBIL according to change in absorbance of the hemoglobin may be obtained, and a correlation therebetween may be deduced.

Figure 4:
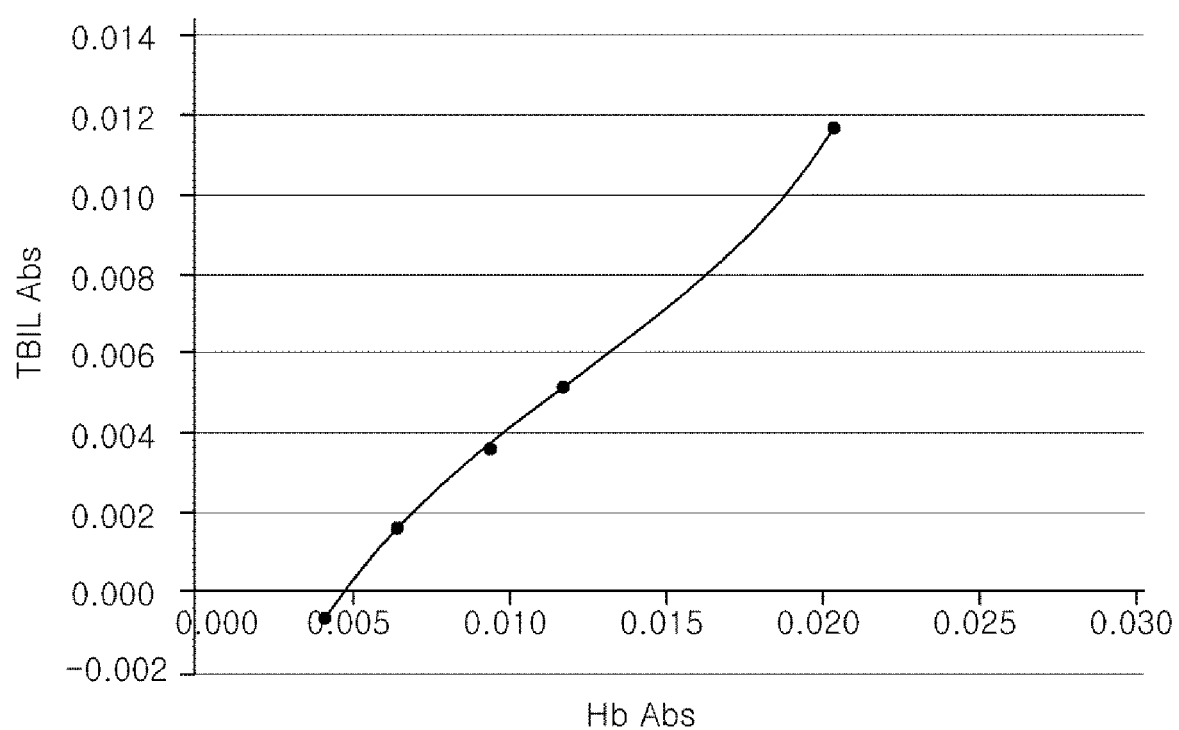
FIG. 4 is a graph showing variation of absorbance of a target according to change in absorbance of hemoglobin.

FIG. 4 is a graph showing the obtained variation of the absorbance of the TBIL according to change in absorbance of the hemoglobin.

Referring to FIG. 4, it can be confirmed that, as the absorbance of the hemoglobin increases, the variation of the absorbance of the TBIL increases.

The correlation between the variation of the absorbance of the target and the absorbance of the hemoglobin, which has been determined through the above-described process, is pre-stored in the storage unit, and the controller 30 calculates the variation of the absorbance of the target by applying the absorbance of the hemoglobin obtained using the equation for calculating the absorbance of the hemoglobin to the correlation.

After measuring the absorbance of the hemoglobin contained in serum and the absorbance of the target and calculating the variation of the absorbance of the target by applying the calculated absorbance of the hemoglobin to the correlation, through the above-described processes, the controller 30 calculates the absorbance of the target that is not affected by hemoglobin that may be contained in serum by subtracting the variation of the absorbance of the target from the measured absorbance of the target. The controller 30 finally calculates the concentration of the target through the corrected absorbance of the target.

Figure 5:
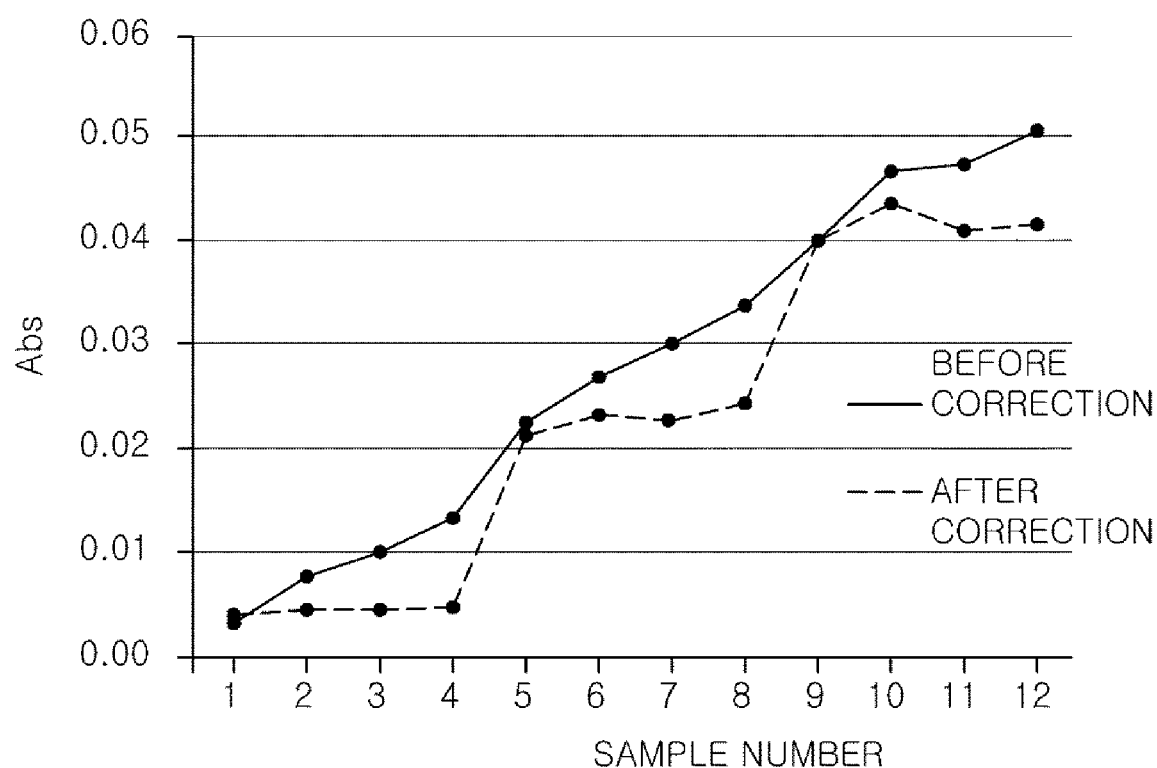
FIG. 5 is a graph showing a comparison between absorbances of a target before and after correction for an impact of hemoglobin.

FIG. 5 is a graph showing a comparison between absorbances of targets before and after correction for an impact of hemoglobin, and Table 5 below shows data shown in plots of FIG. 5.

TABLE 1

| Sample No. | Target concentration (TBIL concentration) | Hemoglobin concentration |
|---|---|---|
| 1 | low | 0 |
| 2 | low | 50 |
| 3 | low | 100 |
| 4 | low | 150 |
| 5 | mid | 0 |
| 6 | mid | 50 |

TABLE 1-continued

| Sample No. | Target concentration (TBIL concentration) | Hemoglobin concentration |
|---|---|---|
| 7 | mid | 100 |
| 8 | mid | 150 |
| 9 | high | 0 |
| 10 | high | 50 |
| 11 | high | 100 |
| 12 | high | 150 |

Referring to Table 1, targets contained in sample nos. 1 to 4 have the same concentration that is lower than the concentrations of targets contained in sample nos. 5 to 12. In addition, the concentration of hemoglobin contained in each sample increases as sample number increases from 1 to 4.

Targets contained in sample Nos. 5 to 8 have the same concentration that is higher than the concentration of the targets contained in sample nos. 1 to 4 and lower than the concentration of targets contained in sample nos. 9 to 12. In addition, the concentration of hemoglobin contained in each sample increases as sample number increases from 5 to 8.

The targets contained in sample nos. 9 to 12 have the same concentration that is higher than the concentrations of the targets contained in sample nos. 1 through 8. In addition, the concentration of hemoglobin contained in each sample increases as sample number increases from 9 to 12.

Referring to FIG. 5, it can be confirmed that the absorbance of TBIL of the samples before correction for an impact of hemoglobin increases according to an increase in concentration of hemoglobin despite the samples containing the same concentration of TBIL.

However, the absorbance of TBIL of the samples having been subjected to the above-described correction process exhibits a trend such that a group of the samples containing the same concentration of TBIL shows almost the same absorbance of TBIL. That is, it can be confirmed that unlike the samples before correction for an impact of hemoglobin, the impact of hemoglobin contained in each sample is mostly removed.

For example, as for the sample nos. 1 to 4 containing the same concentration of the target, as illustrated in a plot before correction of FIG. 5, the absorbance of the target increases as sample number increases, i.e., the concentration of hemoglobin contained in the samples increases. However, as illustrated in a plot after correction of FIG. 5, it can be confirmed that the absorbance of the target is constant even though sample number increases, i.e., the concentration of hemoglobin contained in the samples increases.

Figure 6:
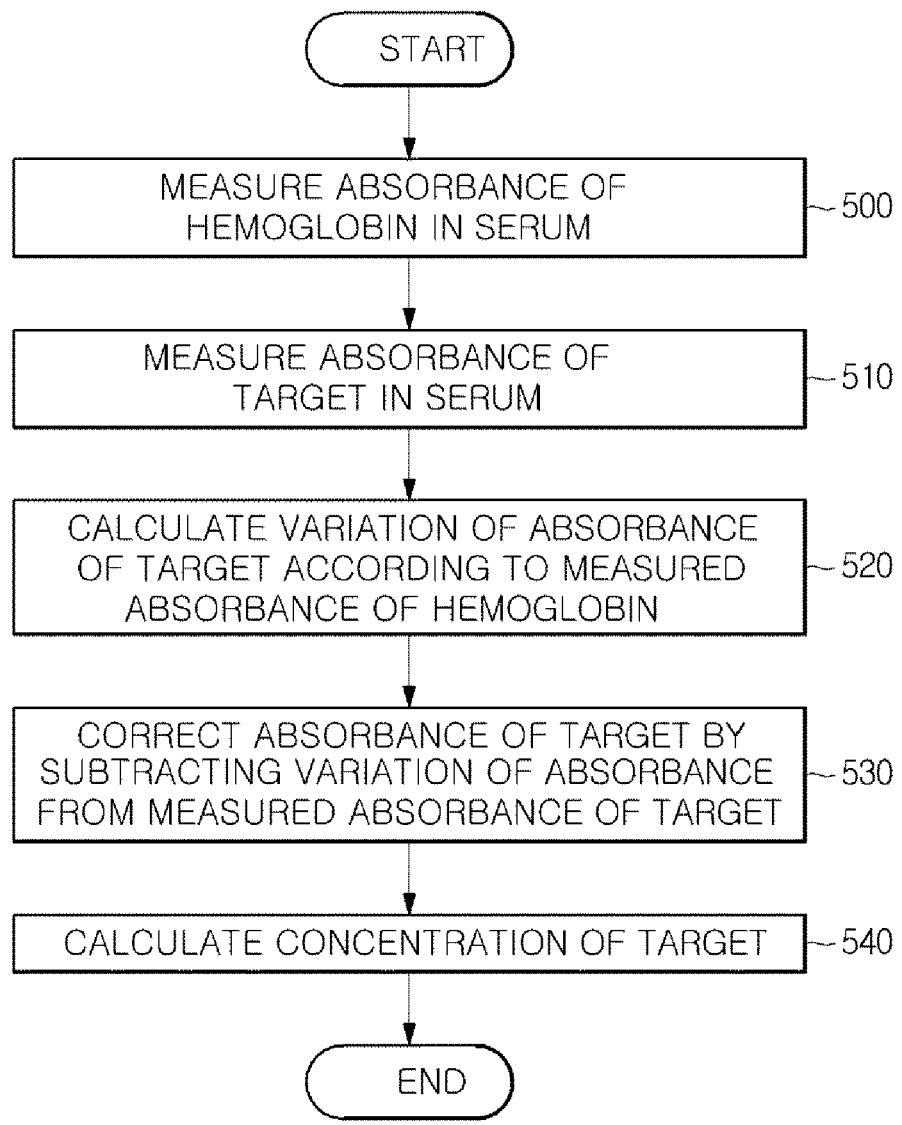
FIG. 6 is a flowchart illustrating a target measurement method according to an exemplary embodiment.

FIG. 6 is a flowchart illustrating a target measurement method according to an exemplary embodiment.

Referring to FIG. 6, the controller 30 measures absorbance of hemoglobin contained in serum (operation 500). In particular, the serum is transferred to the reaction chamber 122 containing a reagent for measurement of TBIL and the control chamber 123, and the controller 30 controls the light emitter 41 of the light detection module 40 to irradiate the control chamber 123 with light having a predetermined wavelength, for example, light having at least one wavelength selected from among 450 nm, 535 nm, and 630 nm.

The light receiver 43 of the light detection module 40 detects light that has passed through the serum contained in the control chamber 123 and transmits detection results to the controller 30, and then the controller 30 uses an equation to calculate the absorbance of the hemoglobin based on the detection results. For example, the controller 30 may calculate the absorbance of the hemoglobin that is minimally affected by the target by applying the absorbance of the control chamber 123 which is detected by the light receiver 43 of the light detection module 40 to the equation for calculating the absorbance of the hemoglobin represented by Equation 1 above.

The controller 30 measures absorbance of the target contained in the serum (operation 510). In particular, the controller 30 controls the light emitter 41 of the light detection module 40 to irradiate the reaction chamber 122 containing a reagent for measurement of TBIL with light having a predetermined wavelength, for example, light having at least one wavelength selected from among 450 nm, 535 nm, and 630 nm.

The light receiver 43 of the light detection module 40 detects light that has passed through the serum accommodated in the reaction chamber 122 and transmits detection results, and then the controller 30 calculates the absorbance of the target based on the detection results. The calculated absorbance of the target includes an impact of the hemoglobin and thus is subjected to a correction process for removal of the impact of the hemoglobin to obtain reliable results.

Next, the controller 30 calculates a variation of the absorbance of the target according to the absorbance of the hemoglobin, which is obtained through the above-described process (operation 520). In particular, the controller 30 calculates the variation of the absorbance of the hemoglobin by applying the calculated absorbance of the hemoglobin to a correlation between the variation of the absorbance of the target and the absorbance of the hemoglobin. The correlation may pre-stored in the storage unit and may be determined through the processes described above.

The controller 30 corrects the absorbance of the target by subtracting the calculated variation of the absorbance of the target from the measured absorbance of the target (operation 530), and calculates the concentration of the target based on the corrected absorbance of the target (operation 540).

After calculating the variation of the absorbance of the target by applying the absorbance of the hemoglobin calculated through the above-described process to the correlation, the controller 30 calculates absorbance of the target that is not affected by hemoglobin that may be contained in serum by subtracting the variation of the absorbance of the target from the measured absorbance of the target. The controller 30 finally calculates the concentration of the target through the corrected absorbance of the target.

According to the exemplary embodiments, more accurate detection results may be obtained by correcting an error in target measurement results by hemoglobin.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A target measurement method comprising:
   measuring an absorbance of hemoglobin in a sample;
   measuring an absorbance of a target in the sample;
   determining a variation of the absorbance of the target according to the measured absorbance of the hemoglobin; and
   correcting the absorbance of the target by subtracting the determined variation of the absorbance of the target from the measured absorbance of the target,
   wherein the determining the variation of the absorbance of the target comprises determining the variation of the absorbance of the target according to the measured absorbance of the hemoglobin based on a pre-determined correlation showing the variation of the absorbance of the target according to the absorbance of the hemoglobin.

2. The target measurement method according to claim 1, wherein the measuring the absorbance of hemoglobin comprises:
   irradiating the sample with light to measure an absorbance of the sample; and
   determining the absorbance of hemoglobin in the sample based on the measured absorbance of the sample and a pre-determined equation for calculation of the absorbance of the hemoglobin.

3. The target measurement method according to claim 2, wherein the irradiating the sample comprises irradiating a sample accommodated in a chamber of a reactor, excluding a reagent for detection of the target, with light having at least one predetermined wavelength.

4. The target measurement method according to claim 3, wherein the reactor comprises:
   at least one reaction chamber; and
   a control chamber excluding the reagent.

5. The target measurement method according to claim 2, wherein the determining the absorbance of the hemoglobin comprises determining the absorbance of the hemoglobin based on the pre-determined equation for calculation of the absorbance of the hemoglobin independently from change in concentration of the target, when measurement results of the absorbance of the sample are input.

6. The target measurement method according to claim 4, wherein the pre-determined equation for calculation of the absorbance of the hemoglobin comprises a variable to be substituted with the absorbance obtained by irradiating the sample accommodated in the control chamber with the light having the at least one predetermined wavelength and a coefficient for calculation of the absorbance of the hemoglobin independently from change in concentration of the target.

7. The target measurement method according to claim 1, wherein the measuring the absorbance of the target comprises measuring the absorbance of the target in the sample by irradiating the sample accommodated in a chamber of a reactor, containing a reagent for detection of the target, with light having at least one predetermined wavelength.

8. The target measurement method according to claim 1, further comprising determining a concentration of the target based on the corrected absorbance of the target after the absorbance of the target is corrected.

9. The target measurement method according to claim 1, wherein the sample comprises blood plasma or serum.

10. The target measurement method according to claim 3, wherein a wavelength of light irradiated to the sample is at least one of 450 nm, 535 nm, and 630 nm.

11. The target measurement method according to claim 3, wherein the irradiating the sample with the light to measure the absorbance of the sample comprises:
    determining a wavelength of light such that change in the absorbance of the hemoglobin according to change in concentration of the target is minimized.

12. The target measurement method according to claim 10, wherein the pre-determined equation for calculation of the absorbance of the hemoglobin determines a coefficient such that change in the absorbance of the hemoglobin according to change in concentration of the target is minimized.

13. The target measurement method according to claim 1, wherein the correcting the absorbance of the target comprises:
- obtaining the variation of the absorbance of the target according to a concentration of the hemoglobin based on the pre-determined correlation between the absorbance of the hemoglobin and the absorbance of the target; and
- correcting the absorbance of the target by subtracting the determined variation of the absorbance of the target from the measured absorbance of the target based on the variation of the absorbance of the target according to the concentration of the hemoglobin.

* * * * *